(12) United States Patent
Cho

(10) Patent No.: US 12,083,306 B2
(45) Date of Patent: Sep. 10, 2024

(54) HIGH-DENSITY MICRONEEDLE

(71) Applicant: LABNPEOPLE CO., LTD., Gyeonggi-do (KR)

(72) Inventor: Sung Youn Cho, Gyeonggi-do (KR)

(73) Assignee: LABNPEOPLE CO., LTD., Gyeonggi-Do (KR)

( * ) Notice: Subject to any disclaimer, the term of this patent is extended or adjusted under 35 U.S.C. 154(b) by 1142 days.

(21) Appl. No.: 16/767,117

(22) PCT Filed: Nov. 28, 2018

(86) PCT No.: PCT/KR2018/014810
§ 371 (c)(1),
(2) Date: May 27, 2020

(87) PCT Pub. No.: WO2019/117510
PCT Pub. Date: Jun. 20, 2019

(65) Prior Publication Data
US 2020/0398034 A1    Dec. 24, 2020

(30) Foreign Application Priority Data

Dec. 11, 2017 (KR) ........................ 10-2017-0169505

(51) Int. Cl.
*A61M 37/00* (2006.01)
*A61L 31/02* (2006.01)
*A61L 31/14* (2006.01)

(52) U.S. Cl.
CPC ....... *A61M 37/0015* (2013.01); *A61L 31/022* (2013.01); *A61L 31/148* (2013.01); *A61L 2300/102* (2013.01); *A61M 2037/0023* (2013.01); *A61M 2037/0038* (2013.01)

(58) Field of Classification Search
CPC ...... A61M 37/0015; A61M 2037/0023; A61M 2037/0038; A61M 2037/0046; A61M 2037/0053; A61L 31/022; A61L 31/148
See application file for complete search history.

(56) References Cited

U.S. PATENT DOCUMENTS

| | | | |
|---|---|---|---|
| 6,050,988 A * | 4/2000 | Zuck | A61N 1/303 604/20 |
| 6,689,100 B2 * | 2/2004 | Connelly | A61M 37/0015 604/289 |
| 2015/0374967 A1 | 12/2015 | Fudoji et al. | |

FOREIGN PATENT DOCUMENTS

| | | |
|---|---|---|
| EP | 1911488 A2 | 4/2008 |
| JP | 2006345983 A | 12/2006 |
| KR | 1019950016794 A | 7/1995 |
| KR | 100572539 B1 | 4/2006 |
| KR | 1020110065391 A | 6/2011 |
| KR | 1020140105686 A | 9/2014 |
| KR | 1020150084806 A | 7/2015 |
| KR | 1020170115431 A | 10/2017 |
| WO | 2014187338 A1 | 11/2014 |
| WO | 2017176077 A1 | 10/2017 |

* cited by examiner

*Primary Examiner* — Bradley J Osinski
(74) *Attorney, Agent, or Firm* — HAUPTMAN HAM, LLP

(57) ABSTRACT

A high-density microneedle of the present disclosure includes: a sheet portion attached to skin; a substrate portion arranged on the sheet portion; and a plurality of insertion pieces arranged on the substrate portion, wherein the substrate portion is arranged on the sheet portion while having a plurality of layers formed therein.

4 Claims, 6 Drawing Sheets

//HIGH-DENSITY MICRONEEDLE

RELATED APPLICATIONS

The present application is a national phase of International Application Number PCT/KR2018/014810, filed Nov. 28, 2018, which claims priority to Korean Application Number 10-2017-0169505, filed Dec. 11, 2017.

TECHNICAL FIELD

The present disclosure relates to a high-density microneedle which is inserted into the skin of a user to deliver active substances that are useful medically, pharmaceutically, or cosmetically to the body.

BACKGROUND ART

A drug delivery system (DDS) is a series of techniques that deliver substances with pharmacological activity to cells, tissues, organs, etc. using various physicochemical techniques.

As the DDS, the oral administration method of ingesting drugs by mouth is most commonly used, and the transdermal injection method in which liquid drugs are delivered to a part of the human body is also widely used. Among the methods, a method of delivering liquid drugs by puncturing on a patient's skin with a metal needle, that is, a method of delivering liquid drugs by using a syringe, has been widely used for a long time.

However, in the drug delivery method using a syringe, when liquid drugs are injected into the body, a patient feels pain, there is a hassle of repeated inoculations, and infection to the patient may be caused by reuse of a needle due to neglect of the administration of a syringe.

In this method, trained persons with knowledge of syringe use are required, so that the patient cannot administer liquid drugs by itself.

Recently, in order to improve the liquid drugs delivery method using a syringe, a micro-sized transdermal injection microneedle that is smaller than a pen-type syringe has been manufactured and used.

Microneedles are a system used to deliver liquid drugs by physically forming a hole in horny layer of the skin. In 1998, the Prausnitz group at Georgia Tech first developed a microneedle array made of silicon devices by using semiconductor processing technique to propose the possibilities of application for drug delivery, and much research thereon has been carried out. Microneedles are made of various materials such as silicon, metal, high polymers, glass, ceramic, etc. and formed into various sizes and shapes.

Microneedles are used for the delivery of active substances such as liquid drugs, vaccines, etc. into the body and the detection and biopsy of analytes in the body, and for injecting skin beauty substances or liquid drugs into the skin tissue or for extracting body fluid such as blood from the inside of the skin. Accordingly, the microneedles capable of injecting liquid drugs locally and continuously and minimizing pain when a needle is inserted into the skin are one of the drug delivery methods that have been rapidly used in various fields in recent years.

However, conventional microneedles have a structure in which liquid drugs are not quickly diffused into the body through the horny layer of the skin. As shown in FIG. 7, a conventional microneedle 10 includes a substrate 1 attached to the skin while being placed on a adhesive sheet (not shown) and needles 2 protruding from the substrate 1 and being inserted into the skin. The needles 2 have a simple structure in which a plurality of needles are arranged on the substrate 1 by being spaced apart from each other a predetermined distance, so that drug diffusion using transdermal is inefficiently performed.

Recently, in order to increase drug delivery rate, methods for enhancing transdermal drug delivery by using chemical enhancer, iontophoresis, electroporation, ultrasound, and thermal devices have been developed, but these methods complicate the manufacturing process of microneedles and increase the manufacturing costs. Further, the above-mentioned methods are often not suitable depending on the types of liquid drugs and may cause side effects on the skin.

Generally, the substrate 1 of the conventional microneedle 10 is manufactured by using a mold. The substrate 1 manufactured by the molding method is pressed by a press device as a post process, and at the same time, the plurality of needles 2 formed on the substrate 1 may protrude by being bending from the substrate 1 under pressure of the press.

However, as described above, the conventional microneedle 10 has a structure in which the plurality of needles 2 is arranged on the substrate 1 by being spaced from each other a predetermined distance. Therefore, the press device should be equipped with a moving mold of a complicated structure, that is, a moving mold having pressing pieces in contact with the plurality of needles 2, respectively.

When the press device having the moving mold presses the plurality of needles 2, portions of the substrate 1 which are arranged between the plurality of needles 2 may be deformed or damaged under influence of the pressing pieces.

In particular, when the number of the needles 2 on the substrate 1 is increase to efficiently deliver liquid drug, the needles 2 are arranged to allow gaps therebetween to become very fine, so the portions of the substrate 1 between the needles 2 may be deformed or damaged under the influence of the pressing pieces.

Accordingly, the present applicant has proposed the present disclosure in order to solve the above problems, and as related art documents thereof, Korean Patent Application Publication No. 10-2014-0105686 'Microneedle patch of stimulating meridian points' has been proposed.

DISCLOSURE

Technical Problem

Accordingly, the present disclosure has been made keeping in mind the above problems occurring in the related art, and an objective of the present disclosure is to provide a high-density microneedle, which is configured to allow active substances useful to the human body to quickly penetrate and be diffused into the skin.

Another objective of the embodiment of the present disclosure is to provide a microneedle in which the number and the density of needles inserted into a predetermined area of the skin are significantly increased in comparison with the conventional microneedle.

A further objective of the embodiment of the present disclosure is to provide a microneedle, wherein needles may be formed without using a molding method by a press.

Technical Solution

In order to accomplish the above object, the present disclosure provides a high-density microneedle. The high-density microneedle of the present disclosure includes: a sheet portion attached to skin; a substrate portion arranged on the sheet portion; and a plurality of insertion pieces arranged on the substrate portion, wherein the substrate portion may be arranged on the sheet portion while having a plurality of layers formed therein.

The substrate portion may have the plurality of layers formed by winding or bending a tape-shaped plate.

The plurality of insertion pieces may be provided at one side of the plate in a width direction thereof and be arranged along a longitudinal direction thereof while being spaced apart from each other by a predetermined distance.

The plurality of insertion pieces may be arranged on a plane that may be a same level as a surface formed by the plate.

The substrate may be provided on the sheet portion while having a circular or polygonal shape.

A plurality of impregnated grooves may be provided at the side of the plate in the width direction thereof, the plurality of impregnating grooves being configured to be impregnated with liquid drugs or active substances.

The sheet portion may have a seating depression in which the substrate portion may be seated.

The substrate portion or the insertion pieces may be made of a bioabsorbable metal.

The bioabsorbable metal may include at least one of magnesium, calcium, zinc, and iron.

Advantageous Effects

As described above, in the high-density microneedle according to the embodiment of the present disclosure, the plurality of insertion pieces is arranged to be dense in an area of the preset sheet portion by a structure of the substrate portion having the plurality of layers, so that the liquid drugs or active substances impregnated in the insertion pieces can be intensively delivered and diffused into the body of a user.

In the multi-type high-density microneedle according to the embodiment of the present disclosure, there is no need to require a separate process in which the insertion pieces are raised up in a vertical direction on the substrate portion, so that it is possible to prevent deformation or damage to the substrate portion or the insertion pieces under the pressure of a press, and as a result, the manufacturing process of the high-density microneedle can be simplified thereby reducing the manufacturing costs thereof.

The high-density microneedle according to the embodiment of the present disclosure is configured to have a plurality of needles without using a moving molding by the press, so that the processing costs of the high-density microneedle can be reduced thereby reducing the overall manufacturing costs thereof.

The high-density microneedle according to the embodiment of the present disclosure is configured to deliver substances (magnesium, calcium, zinc, iron, etc.) included in the bioabsorbable metal into the body in addition to the liquid drugs or active substances, so that beneficial substances such as minerals can be supplied directly into the skin of the user.

MODE FOR INVENTION

Features and advantages of the present disclosure and an achieving method therefor will be more clearly understood from the embodiments, as will be described in detail hereinafter, in conjunction with the accompanying drawings.

However, the present disclosure is not limited to the embodiment disclosed below, but may be implemented in various different forms, the embodiment is provided to make the disclosure of the present disclosure complete, and is provided to fully inform one of ordinary skill in the art to which the present disclosure belongs the scope of the present disclosure, and the scope of the present disclosure is defined by the accompanying claims.

Hereinbelow, a high-density microneedle according to an embodiment of the present disclosure will be described in detail with reference to FIGS. 1 to 5. Prior to the description of the present disclosure, when the functions of conventional elements and the detailed description of elements related to the present disclosure may make the gist of the present disclosure unclear, a detailed description of those elements will be omitted.

Figure 1:
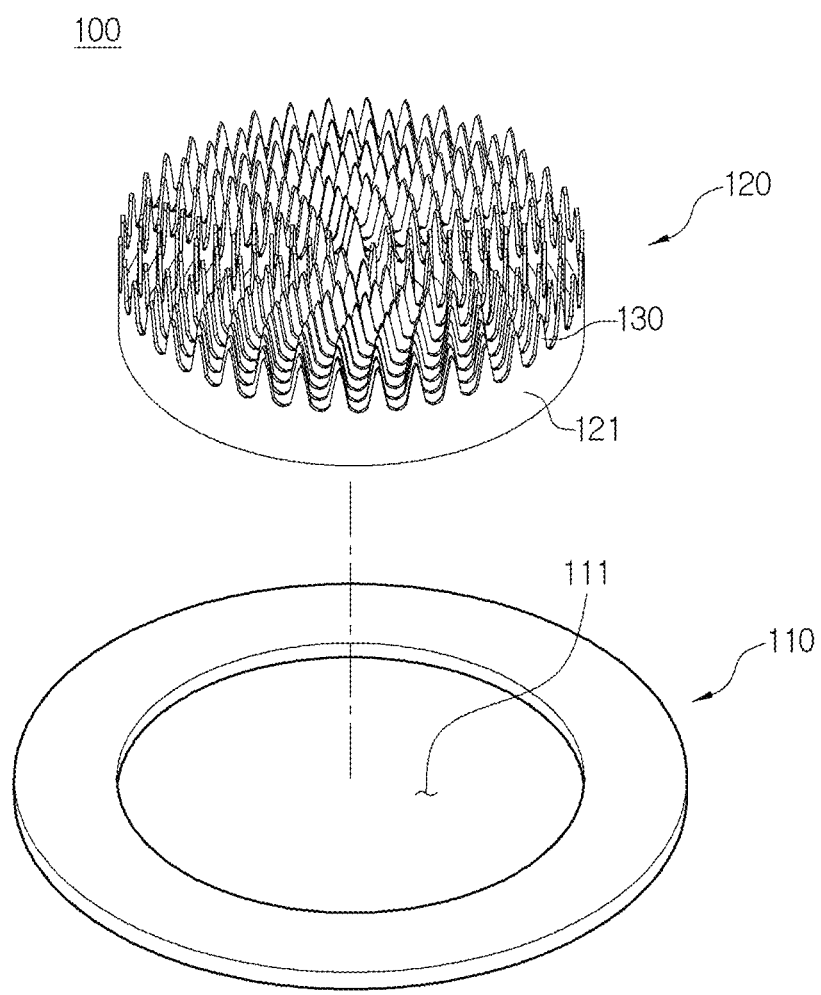
FIG. 1 is an exploded perspective view showing a high-density microneedle according an embodiment of the present disclosure.
Figure 2:
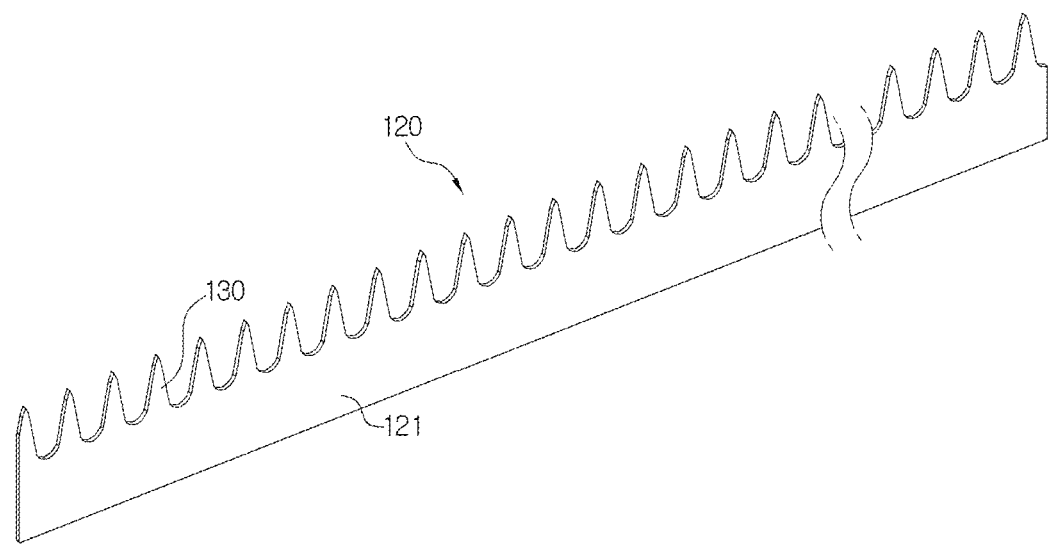
FIG. 2 is a perspective view showing a tape-shaped plate constituting a substrate portion shown in FIG. 1.
Figure 3:
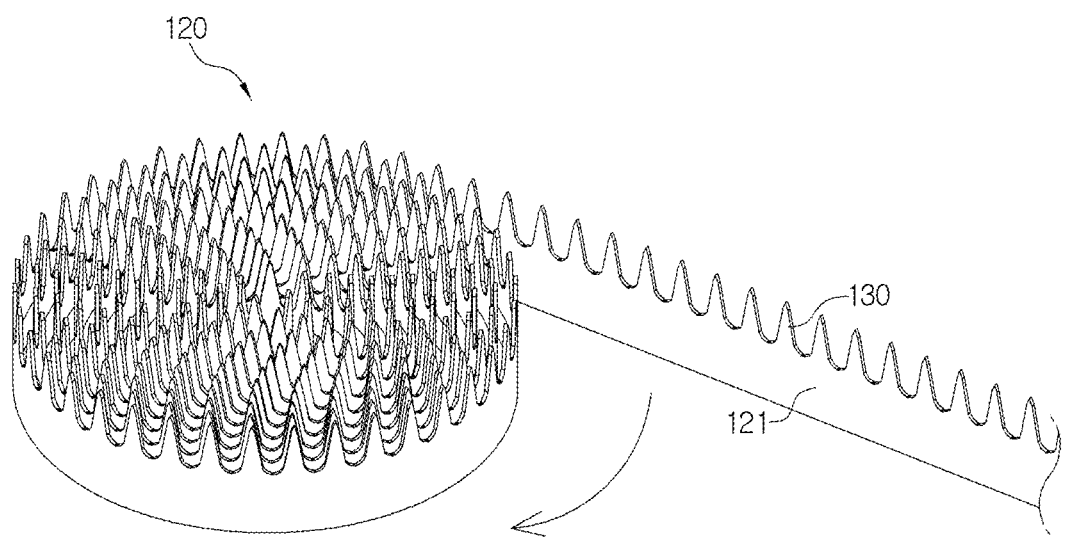
FIG. 3 is a perspective view showing the tape-shaped plate shown in FIG. 2 which is wound to form the substrate portion in a circular shape.
Figure 4:
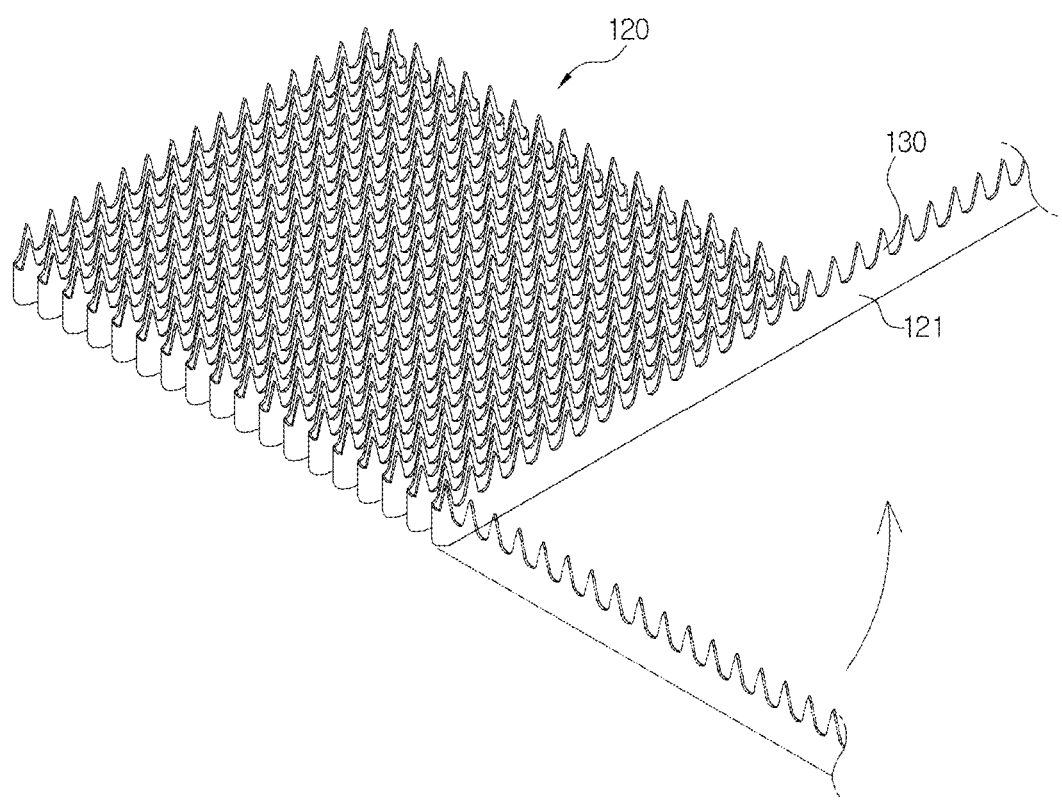
FIG. 4 is a perspective view showing the tape-shaped plate shown in FIG. 2 which is bent to form the substrate portion in a rectangular shape.
Figure 5:
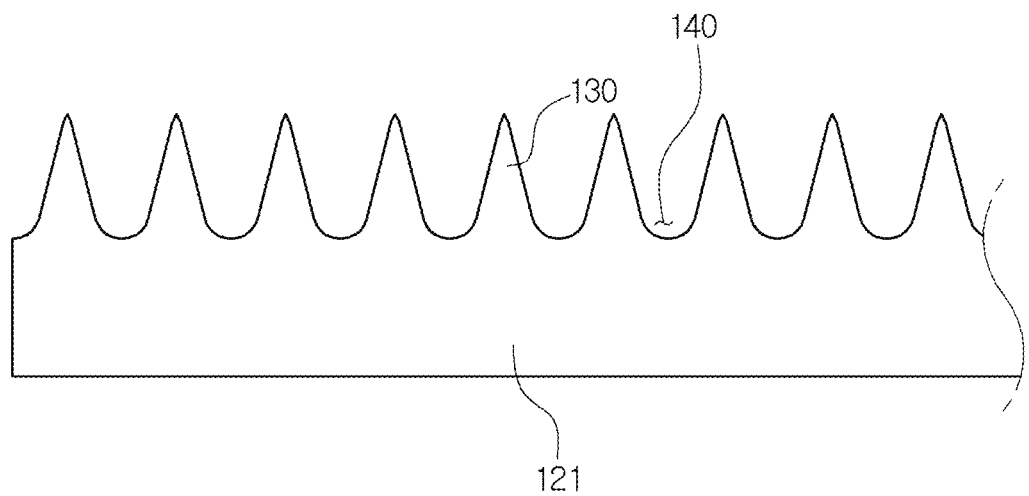
FIG. 5 is a view showing the tape-shaped plate shown in FIG. 2 having a plurality of impregnated grooves.
Figure 6A:
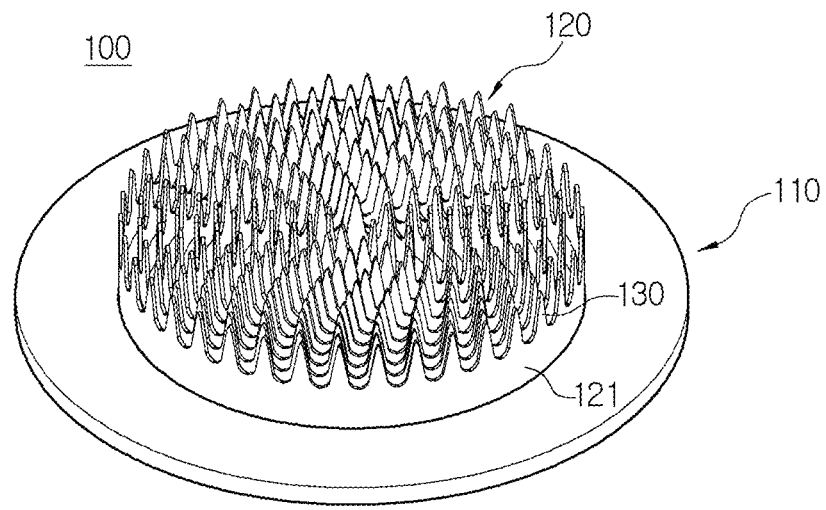
FIGS. 6A and 6B are perspective views showing the high-density microneedle having the substrate portion formed in a circular or a rectangular shape.
Figure 6B:
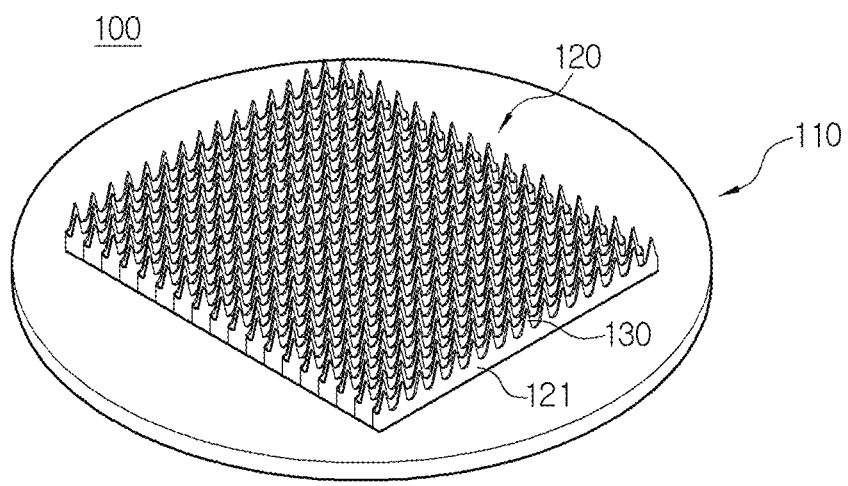
Figure 7:
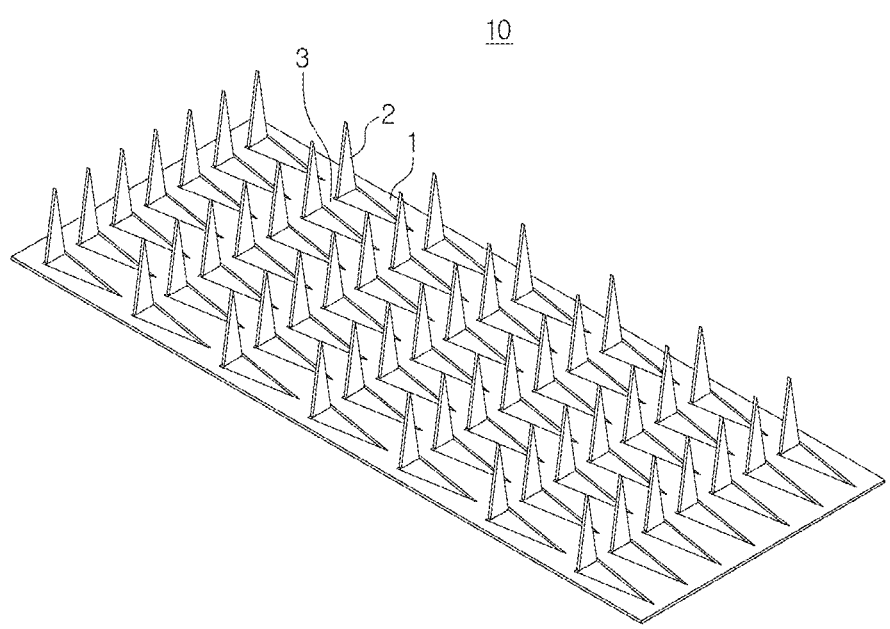
FIG. 7 is a perspective view showing a conventional microneedle.

FIG. 1 is an exploded perspective view showing the high-density microneedle according an embodiment of the present disclosure, FIG. 2 is a perspective view showing a tape-shaped plate constituting a substrate portion shown in FIG. 1, FIG. 2 is a perspective view showing a tape-shaped plate constituting a substrate portion shown in FIG. 1, FIG. 3 is a perspective view showing the tape-shaped plate shown in FIG. 2 which is wound to form the substrate portion in a circular shape, FIG. 4 is a perspective view showing the tape-shaped plate shown in FIG. 2 which is bent to form the substrate portion in a rectangular shape, FIG. 5 is a view showing the tape-shaped plate shown in FIG. 2 having a plurality of impregnated grooves, and FIGS. 6A and 6B are perspective view showing the high-density microneedle having the substrate portion formed in a circular shape or a rectangular shape.

As shown in FIGS. 1 to 5, a high-density microneedle 100 according to an embodiment of the present disclosure may include: a sheet portion 110 attached to skin, a substrate portion 120 arranged on the sheet portion 110, and a plurality of insertion pieces 130 arranged on the substrate portion 120.

The sheet portion 110 may have a predetermined thickness and area and have a circular shape or polygonal shape, and may be replaced with other shapes other than those shown in the drawings, which may function to maintain the substrate portion's shape. For the purpose of expanding the use of attaching the microneedle to skin, etc., on the sheet portion 110, an adhesive material may be applied to remaining areas excluding an area where the substrate portion 120 is provided.

When the sheet portion 110 is attached to skin of a user, the substrate portion 120 is a component in contact with the skin of the user who wants to receive liquid drugs or active substances, and the substrate portion 120 may be arranged on the center of the sheet portion 110 while having a plurality of layers provided therein.

As shown in FIG. 2, the substrate portion 120 is manufactured from a tape-shaped plate 121. That is, the substrate portion 120 may have the circular shape or polygonal shape having the plurality of layers formed by winding or bending the plate 121. The layers may refer to the plate 121.

For example, as shown in FIG. 3, when the plate 121 is wound in a roll shape, the substrate portion 120 may have the circular shape in which the plurality of layers is provided.

That is, when a first end of the plate 121 in a longitudinal direction thereof is centered on the circle and a second end thereof is wound in the circular shape around the first end of the plate 121, the substrate portion 120 may be manufactured in the circular shape having the plurality of layers therein.

For example, as the plate 121 is wound in the roll shape, the substrate portion 120 is illustrated in the description and the drawings as having the circular shape, but is not limited thereto and may have the polygonal shape. The first end of the plate 121 in the longitudinal direction may be centered on the center of the polygonal shape and the second end thereof may be bent at a predetermined angle around the first end thereof to wind the plate in the shape of a rectangle, triangle, etc. Accordingly, the substrate portion 120 may be manufactured in the polygonal shape having the plurality of layers.

As shown in FIG. 4, when the plate 121 is bent by a predetermined distance and layered, the substrate portion 120 may have the rectangular shape in which the plurality of layers is formed.

That is, when the plate 121 is bent by the predetermined distance and layered in zigzag, the substrate portion 120 may be manufactured in the rectangular shape having the plurality of layers.

For example, the plate 121 may impregnated with liquid drugs or active substances that are delivered into the user's skin. As a method of impregnating the plate 121 with liquid drugs or active substances, various known methods, such as a method of impregnating the plate 121 into a container storing liquid drugs or active substances to coat the plate 121 or a method of applying liquid drugs or active substances to the plate 121 to coat the plate 121, etc., may be applied thereto.

The liquid drugs impregnated on the plate 121 may be intended for disease prevention and treatment and may not be limited thereto, and may be a genetic material, epidermal growth factor (HGF) for skin care, or hyaluronic acid.

The substrate portion 120 manufactured as described above may be inserted in a seating depression 111 provided in the sheet portion 110.

The seating depression 111 has a shape corresponding to the shape of the substrate portion 120, and when the substrate portion 120 is seated therein, the seating depression 111 presses a portion of the plate 121, which is arranged at the outermost portion of the substrate portion 120, to prevent the plate 121 from being released. Preferably, the substrate portion 120 may be coupled to the seating depression 111 in a forcible fitted manner.

The plurality of insertion pieces 130 may refer to components that are inserted into the skin of the user to deliver the liquid drugs or the active substances into the skin when the sheet portion 110 is attached to the skin of the user.

The plurality of insertion pieces 130 is integrally connected to the plate 121 of the substrate portion 120 in a single body. As shown in FIGS. 2 and 5, the plurality of insertion pieces 130 may be provided at one side of the plate 121 in a width direction thereof while being arranged along a longitudinal direction of the plate 121 to be spaced apart from each other by a predetermined distance.

A first end of each insertion piece 130 in a longitudinal direction thereof is integrally connected to the side of the plate 121 in the width direction thereof, and a second end of the insertion piece 130 in the longitudinal direction thereof may be a free end that extends horizontally. Preferably, the insertion piece 130 may have an arrowhead shape as a whole to be easily inserted into the skin of the user. The insertion piece 130 has a shape of gradually narrowing in width thereof from the first end of the insertion piece 130 in the longitudinal direction thereof to the second end thereof.

The plurality of insertion pieces 130 may be arranged on a plane that is the same level as a surface formed by the plate 121. The plate 121 and the plurality of insertion pieces 130 may have the same horizontal plane. The plurality of insertion pieces 130 may be inserted into the user's skin while being arranged on the same plane as the plate 121.

Accordingly, in order to insert the plurality of insertion pieces 130 into the user's skin, there is no need to bend the plurality of insertion pieces 130 perpendicularly on the surface of the substrate portion 120 by the molding process or the pressing process using a press device.

Therefore, it is possible to prevent problems such as a problem that occurs when the plurality of insertion pieces 130 are bent on the substrate portion 120 perpendicularly, for example, a problem in that a portion of the substrate portion 120 which supports the end of the insertion piece 130 in the longitudinal direction thereof is deformed or damaged, or a problem in that the insertion piece 130 is pressed by a pressure piece and is cut from the substrate portion 120.

The plurality of insertion pieces 130 is impregnated with the liquid drugs or active substances to be delivered into the user's skin, and an impregnated method may be the same as a method of impregnating the plate 120 with the liquid drugs or active substances.

The plurality of insertion pieces 130 configured as described above is arranged in a predetermined area along a direction of winding or bending the plate 121, so that the liquid drugs or active substances may be efficiently delivered into the user's skin.

The plurality of insertion pieces 130 has a structure formed by extending from the end of the tape-shaped plate 121 in the width direction thereof, not a structure in which the insertion pieces protrude from the flat substrate portion, so that the large number of insertion pieces 130 may be arranged in an area (area where substrate portion is arranged) of the preset sheet portion 110.

In detail, rather than when insertion pieces are arranged on a flat substrate portion by being bent perpendicularly, when the insertion pieces 130 are arranged on the sheet portion 110 having the plurality of layers by using the plate 121, a large number of the insertion pieces 130 may be arranged in the area of the preset sheet portion 110 and spacing between the insertion pieces 130 may become denser.

Accordingly, the high-density microneedle 100 according to the embodiment of the present disclosure is configured to have arrangement in which more of the plurality of insertion pieces 130 is arranged in the predetermined area of the sheet portion 110 than the conventional needle, and to have increased density between the insertion pieces 130, so that the liquid drugs or active substances to be delivered into the body may be delivered and diffused intensively into the user's skin.

According to the embodiment of the present disclosure, the high-density microneedle 100 may include a plurality of impregnated grooves 140 in which the liquid drugs or active substances may be impregnated.

The plurality of impregnated grooves 140 may be provided at the side of the plate 121 in the width direction thereof, the side of the plate 121 being connected with the first end of the insertion piece 130 in the longitudinal direction thereof. Precisely the plurality of impregnated grooves 140 may be provided at a portion of the side of the plate 121 in the width direction, the portion being positioned between the insertion pieces 130 adjacent to each other.

When the plate 121 or the plurality of insertion pieces 130 is impregnated with the liquid drugs or active substances, the plurality of impregnated grooves 140 provides a space storing the liquid drugs or active substances in the form of a solid droplet.

Therefore, when the plurality of insertion pieces 130 is inserted into the user's skin, the liquid drugs or active substances stored in the plurality of impregnated grooves 140 may be delivered into the user's skin along a longitudinal side of the insertion piece 130 while melting by the body temperature of the user. Accordingly, the amount of the liquid drugs or active substances delivered into the body may be controlled. In other words, according to a size of each impregnated groove 140 provided at the plate 121, the amount of the liquid drugs or active substances stored in the plurality of impregnated grooves 140 may be controlled, thereby controlling the amount of the liquid drugs or active substances delivered into the body may be controlled.

It is preferable that the side of the plate 121 in the width direction thereof, which partitions the impregnated grooves 140, may have an inclined surface, as shown in FIG. 5(b). This is because the liquid drugs or active substances to be stored in the plurality of impregnated grooves 140 are easily stored.

The plate 121 and the plurality of insertion pieces 130 integrally connected to the plate 121, which constitute the substrate portion 120, may be made of a bioabsorbable metal. The substrate portion 120 and the plurality of insertion pieces 130 may be made of a metal including at least one of magnesium, calcium, zinc, and iron that are used as the bioabsorbable metal.

Accordingly, not only the liquid drugs or active substances impregnated in the substrate portion 120 or the plurality of insertion pieces 130 may be delivered into the user's skin, but also minerals included in the bioabsorbable metal may be delivered into the user's skin. That is, as magnesium, calcium, zinc, and iron used as the bioabsorbable metal are delivered into the user's skin, minerals may be supplied into the body.

For example, in order to apply the bioabsorbable metal as an orthopedic implant, a magnesium-based alloy has been made and commercialized at home and abroad, the bioabsorbable metal applied to the orthopedic implant has been focused on lowering the decomposition rate thereof in the body or improving corrosion resistance for safe fracture fixation.

However, unlike the bioabsorbable metal applied to orthopedics, the bioabsorbable metal used in the high-density microneedle 100 according to the embodiment of the present disclosure is configured to accelerate the decomposition rate in the body, thereby allowing liquid drugs to be released and mineral to be supplied into the user's skin. Further, an applicable form of a mechanism of liquid drug releasing and mineral supply may be provided by being patterned on the substrate portion 120 or the plurality of insertion pieces 130 by the known lithography or etching technique.

Although the detailed embodiment of the present disclosure has been described for illustrative purposes, those skilled in the art will appreciate that various modifications, additions, and substitutions are possible, without departing from the scope and spirit of the present disclosure.

Accordingly, the present disclosure is intended to cover not only the above-described embodiment, but also various alternatives, modifications, equivalents and other embodiments that may be included within the spirit and scope of the present invention as defined by the appended claims.

The invention claimed is:

1. A high-density microneedle, comprising:
   a sheet portion attachable to skin;
   a substrate portion arranged on the sheet portion; and
   a plurality of insertion pieces arranged on the substrate portion, wherein
   the substrate portion is arranged on the sheet portion while having a plurality of layers formed therein,
   the substrate portion has the plurality of layers formed by winding or bending a tape-shaped plate,
   the plurality of insertion pieces is provided at one side of the tape-shaped plate in a width direction of the tape-shaped plate, and is arranged along a longitudinal direction of the tape-shaped plate while being spaced apart from each other by a predetermined distance,
   a plurality of grooves configured to be impregnated with liquid drugs or active substances is provided between the plurality of insertion pieces,
   the sheet portion has a seating depression in which the substrate portion is seated,
   the seating depression has a shape corresponding to a shape of the substrate portion,
   the seating depression is configured to, when the substrate portion is seated in the seating depression, press a portion of the tape-shaped plate, which is arranged at an outermost portion of the substrate portion,
   the seating depression is a single depression configured to receive the substrate portion in entirety,
   the tape-shaped plate is wound in a roll shape to form the plurality of layers, and
   among the plurality of layers, a first layer is in contact with a second layer adjacent to the first layer in a radial direction of the substrate portion.

2. The high-density microneedle of claim 1, wherein the plurality of insertion pieces is arranged on a plane that is a same level as a surface formed by the tape-shaped plate.

3. The high-density microneedle of claim 1, wherein the substrate portion or the plurality of insertion pieces is made of a bioabsorbable metal.

4. The high-density microneedle of claim 3, wherein the bioabsorbable metal includes at least one of magnesium, calcium, zinc, and iron.

* * * * *